United States Patent
Peddareddigari et al.

(10) Patent No.: US 7,407,672 B2
(45) Date of Patent: Aug. 5, 2008

(54) COMPOSITION DERIVED FROM BIOLOGICAL MATERIALS AND METHOD OF USE AND PREPARATION

(75) Inventors: Vijay Gopal Reddy Peddareddigari, Philadelphia, PA (US); Tai Tian Lim, Singapore (SG); Reida Menshawe El Oakley, Singapore (SG)

(73) Assignees: National Heart Center, Singapore (SG); National University of Singapore, Singapore (SG)

( * ) Notice: Subject to any disclaimer, the term of this patent is extended or adjusted under 35 U.S.C. 154(b) by 676 days.

(21) Appl. No.: 10/288,166

(22) Filed: Nov. 4, 2002

(65) Prior Publication Data

US 2004/0086496 A1 May 6, 2004

(51) Int. Cl.
*A61K 9/14* (2006.01)
*A61K 9/50* (2006.01)
*A61L 15/00* (2006.01)
*C12N 11/00* (2006.01)
*C12N 5/02* (2006.01)

(52) U.S. Cl. .............. 424/520; 424/445; 424/447; 424/484; 424/492; 424/93.2; 435/174; 435/397; 514/944; 524/916

(58) Field of Classification Search .............. None
See application file for complete search history.

(56) References Cited

U.S. PATENT DOCUMENTS

| | | | |
|---|---|---|---|
| 4,526,938 A | 7/1985 | Churchill et al. | 525/415 |
| 4,716,203 A | 12/1987 | Casey et al. | 525/408 |
| 4,741,337 A | 5/1988 | Smith et al. | 128/334 |
| 4,957,744 A | 9/1990 | della Valle et al. | 424/401 |
| 5,162,430 A | 11/1992 | Rhee et al. | 525/54.1 |
| 5,324,775 A | 6/1994 | Rhee et al. | 525/54.2 |
| 5,470,730 A * | 11/1995 | Greenberg et al. | 435/456 |
| 5,498,259 A | 3/1996 | Mourant et al. | 606/8 |
| 5,643,192 A | 7/1997 | Hirsh et al. | 604/4 |
| 5,833,651 A | 11/1998 | Donovan et al. | 604/53 |
| 6,129,705 A | 10/2000 | Grantz | 604/96 |
| 6,159,946 A | 12/2000 | Zalewski et al. | 514/44 |
| 6,197,013 B1 | 3/2001 | Reed et al. | 604/509 |
| 6,310,190 B1 * | 10/2001 | Hansen et al. | 536/23.1 |
| 6,777,000 B2 * | 8/2004 | Ni et al. | 424/488 |

FOREIGN PATENT DOCUMENTS

| | | |
|---|---|---|
| DE | 3214337 | 10/1983 |
| EP | 0 068 149 A2 | 1/1983 |
| EP | 0 485 210 A2 | 5/1992 |

OTHER PUBLICATIONS

Fatah et al (Thromb. Haem. 68(2): 130-135, 1992).*
Koutroubakis et al (J. Clin. Pathol. 56:817-820, 2003).*
Bos et al (Thromb. Haemost. 82: 1757-1763, 1999).*
Ueda et al (Clin. Exp. Immunol. 53: 217-224, 1983).*
Avrameas et al (Immunochem. 6: 53-66, 1969).*
Takahashi et al (Int. Arch. Allergy Appl. Immunol. 48(5): 642-652, 1975).*
Kulkami et al., *Polylactic Acid for Surgical Implants*, Arch Surg, vol. 93, Nov. 1966, p. 839-843.
Domb et al. *Poly(anhydrides), 3. poly(anhyrdrides) Based on Aliphatic-Aromatic Diacids*, Macromolecules 1989, 22, 3200-3204.
Miyake et al, *Solution Properties of Synthetic Polypeptides, XVIII: Helix-Coil Transition of Poly-$N^5$-(2-Hydrozyethl)L-Glutamine*, Biopolymers, vol. I3, 1173-1186 (1974).
Simon J. Holland et al., *Polymers for Biodegradable Medical Devices. 1. The Potential of Polyesters As Controlled Macromolecular Release Systems*, Journal of Controlled Release, 4 (1986), 155-180.
Paul S. Teirstein et al., *Catheter-Based Radiotherapy to Inhibit Restenosis After Coronary Stenting*, The New England Journal of Medicine, Jun. 12, 1977, vol. 336, No. 24, p. 1697-1703.

* cited by examiner

*Primary Examiner*—Richard Schnizer
(74) *Attorney, Agent, or Firm*—Klarquist Sparkman, LLP (57) ABSTRACT

The invention provides a novel composition and methods of its preparation and uses. The composition comprises as main components serum and a gelling agent and is useful in various medical applications. The composition may be used to coat a medical device, as a biological glue, or as dressings, membranes, scaffolding or hydrogel useful in bioengineering applications. One or more therapeutic products may be added to the composition and the composition is also a vehicle for delivery of therapeutic products.

46 Claims, 8 Drawing Sheets

COMPOSITION DERIVED FROM BIOLOGICAL MATERIALS AND METHOD OF USE AND PREPARATION

FIELD OF THE INVENTION

This invention relates to compositions derived from biological materials, comprising as main components serum and a gelling agent and which may be adapted for use in a variety of medical applications.

BACKGROUND OF INVENTION

Human and veterinarian medical and surgical procedures often require the use of various materials and substrates that can be used as implants, scaffolding for tissue growth or repair, wound closures, adhesives or glues, or as delivery mechanisms to deliver genes or drugs to a specific site for localised therapy. The materials should be biologically inert, so as not to react with surrounding tissue. It is also important that the materials are sufficiently strong to perform the required function in the patient's body, while at the same time being relatively flexible.

While the materials or substrates that are to be used as surgical implants or delivery devices are specifically designed for each particular use, such materials tend to have common disadvantages or drawbacks. Materials used for wound closures, stents, or as devices to deliver therapeutic compounds or genes tend to be synthesised from synthetic polymers. Such polymers often are not biodegradable, necessitating either a second procedure to remove the implanted material, or that the material be left permanently in place. Furthermore, due to their synthetic nature, such materials are not fully compatible with the body. That is, there is a risk that the patient may develop an inflammatory or immunological reaction to the implanted material.

As a result, biodegradable polymers have been developed for surgical use and implantation. These include polylactic acid (Kulkarni et al, 1966), polyanhydrides and polyorthoesters (Domb et al, 1989), polyamino acids (Miyake et al, 1974), and polyesters of alpha-hydroxy acids (Holland et al, 1986). U.S. Pat. No. 4,957,774 discloses the cross-linking of hyaluronic acid to produce a biodegradable, swellable plastic polymer. U.S. Pat. No. 4,741,337 discloses a biodegradable, glycolide-rich polymer for use as a wound fastener.

Recent attempts to produce synthetic polymers for use in surgical implants have involved polymers that are more inert and therefore are more capable of interfacing with living tissue in a non-reactive manner. U.S. Pat. No. 4,526,938 discloses the preparation of a synthetic, amphipathic polymer incorporating a therapeutically active peptide that is released upon breakdown of the polymer. The hydrophilic portion of the polymer may not be fully biodegradable. U.S. Pat. No. 4,716,203 discloses the preparation of a synthetic, degradable, water-soluble, thermoplastic block copolymer containing polyglycolic acid and polyethylene glycol. This polymer can be formed into a hydrogel for use as implant material. U.S. Pat. No. 5,162,430 discloses the preparation of a semi-synthetic polymer by cross-linking collagen, a biological polymer, to synthetic hydrophilic polymers such as polyethylene glycol. Semi-synthetic polymers are also disclosed in U.S. Pat. No. 5,324,775, which describes the covalent attachment of biological polymers such as polysaccharides to polyethylene glycol polymers.

These synthetic or semi-synthetic polymers are partially or fully biodegradable, which allows for at least limited dissolution of the implanted material. However, the degradation products may be toxic to surrounding tissue at higher concentrations, and rapid breakdown can lead to harmful localised levels of degradation product. As well, inflammation and cytotoxicity are not fully eliminated with the use of these polymers. Furthermore, the preparation of these polymers requires the use of organic solvents for polymerisation. These solvents are expensive and can be toxic, mutagenic or carcinogenic to tissue at the implant site, as well having a potentially denaturing effect on proteins or drug compounds that may also be delivered to the implant site. Additionally, this requirement for organic solvents to facilitate polymerisation means that these polymers cannot polymerise in vivo.

In order to avoid the problems encountered with synthetic or semi-synthetic polymers, materials derived from biological substances have also been described. EPA 0068149 discloses a web-like material prepared from fibrin and fibrinogen that can be used as a wound covering, bone filler or as a delivery system for therapeutically active compounds. This polymer, while being fully biologically-derived, has the disadvantage of being too rigid, even when in contact with water or biological fluids. This rigidity significantly limits the applications for which this material can be used. German Patent No. 3,214,337 describes a multi-layered sheet material that is composed of glycoprotein layers containing alternatively thrombin or fibrinogen. This separate layering of the thrombin and fibrinogen results in a weaker material, as a cross-linked fibrin web is not generated. EPA 0485210 discloses a collagen membrane that contains fibrin. However, animal-derived collagen can elicit a strong inflammatory response from some patients. Currently, transgenic or recombinant human collagens are extremely expensive to produce.

Surgical techniques often involve the use of adhesives to join severed tissue or bone and to adhere tissue grafts at a surgical site. Conventional techniques involve the use of synthetic glues such as cyanoacrylates. However, these glues are not readily biodegraded, and tend to form an inflexible and relatively weak bond. U.S. Pat. No. 5,643,192 describes fibrin-based materials that are used to form stronger bonds when used as bioglues, and are more readily biodegraded. Fibrin has been shown to support keratinocyte and fibroblast growth at the implant site. However, as with the cyanoacrylates, the fibrin-based materials are not stretchable when polymerised. This lack of elasticity leads to a high rupture-rate for seals formed with these materials, especially when the bonds formed are subject to deformation stress. Other adhesives that use the plasma protein serum albumin together with a multifunctional aldehyde have been developed. These adhesives provide a strong bond, but carry the risk of infection due to the biological source of the blood protein. As well, many of the adhesives currently in use as bioglues tend to cause inflammation at the surgical site due to the high concentration of cross-linking agents they contain.

U.S. Pat. No. 5,498,259 discloses a method of fusing bone by chemically removing a thin layer of the mineral matrix from the surfaces of bone to be joined and then painting the joint with a fluorescent dye and heating the dye using electromagnetic radiation to seal the joint. This process is not suitable for clinical use as it is not performed in an in vivo setting. As well, the strength of the bond is not sufficient for clinical applications.

Various materials are also used in surgical techniques to fill bone cavities, or to replace some or all of an existing bone. One current technique involves the use of polypropylene fumarate ("PPF") as a cross-linked bone replacement matrix. PPF cross-links at low temperatures, possesses high mechanical strength and biodegrades into non-toxic degradation products, making it a suitable material for bone replacement, scaffolding and cement. However, formulations of PPF that incorporate toxic monomers in the PPF polymer, such as a vinyl monomer or N-vinyl pyrrolidine, can result in delivery of toxic impurities to the surgical site if the matrix is not completely polymerised, as well as the release of toxic degradation products upon biodegradation.

Another use of material in medical procedures is as a delivery system for therapeutic products such as DNA, drugs or cells. Material containing the therapeutic product is often coated on surgical implants. Fibrin glue has been used to deliver cultured cells and exogenous growth factors (Currie et al). Fibrin glue may not be ideal for the prevention of restenosis, or renarrowing of blood vessels after surgery, as the presence of residual thrombin in the fibrin glue may induce thrombosis, which may lead to vascular obstruction at the implant site. U.S. Pat. No. 5,83,651 describes the use of fibrin glue coated on stent implants as a method of delivering therapeutic virus.

Various mechanical devices have also been used to deliver therapeutic products to a particular site in the body. Stents that release naked DNA that encodes therapeutic gene products have been used, but this method results in a low rate of transduction of surrounding cells with the therapeutic DNA, as well as transient expression of the therapeutic gene (Klugherz et al). Another approach involves the use of balloon catheters that contain micro-encapsulated spheres of the therapeutic product, as disclosed in U.S. Pat. Nos. 6,129,705 and 6,159,946. This approach has the disadvantage of the balloon catheter causing occlusion of blood flow for considerable lengths of time, creating risk to the patient. U.S. Pat. No. 6,197,013 discloses the use of micropourous metal microneedles that have been coated directly with the therapeutic product to deliver the product into the wall of a blood vessel. The efficacy and safety of the system is yet to be proved comprehensively.

In summary, there is a general need for a material that can be used for various medical and surgical applications that is preferably biodegradable, biologically inert, biocompatible and immunocompatible, and has significantly reduced toxicity. Such a material should ideally be able to rapidly polymerise in situ, be capable of connecting and stabilising tissue in a moist environment and be able to retain strength and flexibility when used as an adhesive or when implanted in a patient. It is also important that the material does not impede proper regeneration of tissue at the implant site.

SUMMARY OF INVENTION

The present invention relates to a composition which may be used in a variety of medical, including surgical procedures. The composition comprises serum and a gelling agent such as gelatin, collagen, starch, dextran, chitosan, cellulose, synthetic polypeptides and the like. The gelling agent is preferably biologically derived. The composition may further comprise an anticoagulant such as heparin, acetylsalicylic acid or its derivatives or other antiplatelet factors. The composition may further comprise a cross-linking or polymerising agent, preferably an aldehyde cross-linking agent. The composition may still further comprise a therapeutic product such as nucleic acid, a drug, growth factors, cells, including stem cells, and viral-packaging cells and viruses. Therefore, in one embodiment, the composition is a delivery vehicle for a therapeutic product. In other embodiments, the composition is a biological glue, dressing, membrane, scaffolding or hydrogel useful in numerous medical applications. One or more additives, agents or components may also be added to the composition to achieve a desired set of characteristics and such additives, agents, or components include preservatives, antimicrobial agents, pigment, stabilizer, plasticizer and binder.

When applied to a medical device, such as a stent, the composition provides an efficient vehicle for delivery of a therapeutic product to a desired site in the body. The term "medical device" is used to describe broadly all articles, prosthetic or otherwise used in surgical and other medical procedures including for implantation. In one aspect, the invention therefore provides a method of delivery of a therapeutic product to a desired site in a body of a patient comprising the steps of adding a therapeutic product to the composition, applying the composition to a medical device either before or after adding the product, and placing the coated device at the site.

The invention also provides novel methods of adhering cells to a medical device. In one aspect, the invention provides a method of adhering cells to a medical device comprising the step of applying a composition according to the invention to the device to form a coat, and culturing the coated device with the cells. In another aspect, the invention provides a method of adhering cells to a medical device comprising the step of mixing the cells with a composition of the invention and then applying the composition to the device to form a coat.

The invention further provides a method of preparing a composition comprising the steps of mixing serum and a gelling agent. In various embodiments, the mixture is gelled and an anti-coagulant such as heparin or a cross-linking agent is added prior to the step of gelling.

The invention further provides a method of coating a medical device comprising the step of applying a composition of the invention to the device to form a coat.

In the most preferred aspect, the composition of the invention is derived from biological materials and the invention provides a biomaterial that is biocompatible, non-toxic and fully biodegradable, and as such is ideal for use in medical applications. Moreover, the composition can be custom-made for each patient (meaning any animal patient, including a human patient) by using autologus serum, ie from the patient's own blood. The term "autologus serum" is used herein to describe serum derived from the patient for whom the composition is intended. The use of autologous serum results in a biomaterial that is not likely to elicit an immunological reaction and that is unlikely to cause inflammation at the surgical site. As well, this eliminates the risk of infection from blood-borne infectious agents such as viruses.

Another advantage is that the composition gels rapidly, is flexible and can polymerise under moist conditions. The composition can therefore provide a strong, flexible material for use as glue, dressings, membranes, scaffold and hydrogel.

DETAILED DESCRIPTION OF INVENTION

The present invention provides a composition that can be adapted for use in a variety of medical, including surgical applications, both human and veterinarian. Specifically, the composition of the invention forms a sticky, biologically-derived substrate that can be modified or adapted so as to provide a material that can be used in a diverse range of surgical, wound-repair, and other therapeutic applications. In one embodiment, the invention provides a composition that may be used to coat a medical device such as a stent. In another embodiment, the composition is biological glue that can be used to join tissues and bones or as a sealant to stop bleeding or blood flow. The composition may also be adapted to provide dressings, membranes, scaffolding or hydrogel useful in bioengineering applications. In all such embodiments, one or more therapeutic products may be added to the composition such that the composition also serves as a delivery vehicle, to deliver therapeutic products in a direct and localised manner, to a surgical site or a wound site in a patient.

The main components of the composition may be derived from biological materials, thereby being biodegradable, biocompatible and non-toxic. As well, the biological nature of the composition reduces the risk of a patient developing an adverse inflammatory or immunological reaction to the composition when used in medical and surgical applications.

The main components of the composition are serum and a gelling agent, preferably a biologically-derived gelling agent such as gelatin, collagen, starch, dextran, chitosan or cellulose. The serum may be autologus to provide a customised composition that further reduces the risk of blood-borne infections and an immunological reaction.

The term serum is used herein to broadly refer to any fluid portion derived from blood of an animal (i.e. without cells), and includes blood serum, plasma, plasma-derived serum or a mixture thereof and which may be a pooled product. The present composition which includes serum as a main component provides a material that is biocompatible, nutritive and minimally immunological and as such is very well suited for use in various medical applications, including as a delivery vehicle for therapeutic cells. Serum contains a large number of proteins and as will be appreciated by those skilled in the art, one or more components may be added or deleted from serum without affecting these properties of serum. The term serum as used herein also refers to any such modified serum. For certain uses of the composition, such modified serum may be advantageous. For example, IgG may be removed in the known manner to reduce immunogenicity of serum and the resulting low IgG serum is particularly preferred if the serum is not autologous. Complement inactivated serum is also advantageous as it reduces risk of inflammation and is particularly preferred if the composition is intended for use at a vascular site.

In one embodiment, the composition comprises about 25-150% (v/v) complement-inactivated serum and about 0.1 to 40% (w/v) gelling agent such as gelatin, collagen, starch, dextran, chitosan, cellulose or synthetic polypeptides. The concentration of serum indicated herein is by initial volume such that 150% serum may be obtained by concentrating serum in the known manner, for example by heating at 65° C. to reduce the volume. To minimize denaturation of protein, serum is preferably concentrated by freezing at −20° C. and lyophilization in vaccum using a lyophilizer at −45° C. for 24 hours. The lyohphilized serum powder can then be reconstituted in plain water to the desired concentration. Preferably, the composition is complement-inactivated serum (ie 100%) comprising about 2 to 10% gelatin. In other embodiments, the serum may be suitably diluted, for example in an isotonic solution such as normal saline (NS) or phosphate buffered saline (PBS). It will be understood that the desired rate of polymerisation, strength of the composition and use of the composition will determine the concentration and the selection of the components of the composition. It will also be understood that the protein concentration in serum varies in different individuals, such that the serum concentration may require adjustment as required, for example by preparing a concentrated serum, or diluting the serum concentration. Blood serum normally contains about 5.5 to 9 gram of total proteins per 100 ml and in one embodiment, the serum contains a total protein concentration of about 5.5 to 9 gram/100 ml. Where the gelling agent is a synthetic polypeptide, the concentration should be lower than 0.1%, preferably about 0.01%.

The composition may further comprise an anti-coagulant such as heparin, low molecular weight heparin, acetylsalicylic acid or its derivatives or other anti-platelet factors. Preferably, the composition comprises heparin at a concentration of 150 to 1000 U/ml, more preferably 250 U/ml. In one embodiment, complement in the serum has been inactivated. Inactivation of complement in the serum and the presence of anti-coagulant such as heparin minimise any risk of inflammation and thrombosis.

The composition may be prepared by mixing the serum and a gelling agent and the method of its preparation is another aspect of the invention. In one embodiment, the method further comprises gelling the mixture of serum and the gelling agent. The mixing step may be effected by heating at about 45° C. for about 15 minutes to ensure dissolution of the gelling agent. Heating at about 65° C. for 10 minutes may also be suitable. However, it will be appreciated that if the composition includes any heat sensitive component, the heating temperature should not exceed about 40 to 45° C. The mixture then may be cooled to room temperature to effect gelling. As the serum gels reversibly at temperatures below about 37° C., the gelling step may be effected at a temperature range of about 0° C. to room temperature. As will be understood by those skilled in the art, the rate of gelling will be faster at lower temperature; at about 4° C. the composition will gel in about 5 min; at room temperature of about 24-25° C., in about 10-40 min, depending on the concentration of the gelling agent. In one embodiment, an anti-coagulant such as heparin is added to the mixture, prior to the gelling step, and preferably before any heating step to mix the gelling agent and serum.

In one embodiment, 5% gelatin and 150 to 250 U/ml of heparin are added to complement-inactivated serum. The gelatin and heparin are dissolved by vortexing followed by heating to about 45° C. for about 15 minutes, and then the mixture is cooled to room temperature. The mixture will gel upon standing at room temperature, and gelling should be complete after about 30 minutes at about 25° C. if using 5% gelatin. The mixture can be prevented from gelling by keeping the mixture at a temperature of greater than about 37° C. The gelling rate is directly related to gelatin concentration and inversely related to temperature.

The composition can be used to coat a medical device, for example articles for implantation in the body, such as a stent, to reduce inflammation associated with introduction of a foreign device into the body of a patient. Preferably, multiple coats are applied to such articles by drying each coat prior to application of the next. The coated device is then allowed to dry prior to implantation in a patient. Preferably, three layers of the composition are applied to the device, the composition is dried at about 4° C. for about 1 hour following the application of each of the first two coats, and for ½ hour at room temperature following the application of the third coat. Application of the composition may be accomplished in any convenient manner, for example by dipping the devise in the composition for 1 min or by spraying the composition to form a uniform layer. The application of the composition may be carried out at any temperature that permits the composition to be applied. Where a thin layer of the composition is desired, the composition is advantageously applied at 37° C. At temperatures lower than 37° C., the composition is more viscous such that a thicker layer is applied. Moreover, as the temperature decreases, the composition gels more quickly requiring the application of the composition within a shorter period of time.

The composition of the invention may also be used as a delivery vehicle for therapeutic products, including cells. The term "therapeutic product" is used in the broadest sense to refer to all products that are intended for or capable of treatment, prevention or mitigation or amelioration of a disorder or disease, or its symptoms. The composition can maintain live cells and is therefore particularly suited as a delivery vehicle or carrier for therapeutic cells. Therapeutic cells suspended in the composition (in liquid form) may be delivered to a particular site by injection, for example ex-myoblast or stem cells suspended in the composition may be injected into muscle or heart. Since the composition is viscous and sticky, it will act to keep the cells at the site of injection. In another embodiment, the composition in liquid form can be used to transport and store cells.

The composition when applied to a medical device also serves as a vehicle for delivery of therapeutic products to a desired site in the body. In this aspect of the invention, a therapeutic product such as cells, nucleic acid, drugs, growth factors and other therapeutically effective chemicals or biochemicals may be added to the composition either before or after the composition is applied to a device and delivered to a desired site by placing the device coated with the composition at the site. For example, cells producing therapeutic factors or drugs, proteins or genes, when coated onto a stent in accordance with the invention may be delivered to an intravascular site to strengthen aneurysmal vessels or varicose vein as well as treat vascular malformations like hemangiomas, lymphatic disorders and other vascular disorders. Moreover, cell coated devices such as stents releasing viruses with suicide or other genes may be delivered to a desired site in the body to treat malignancies. For example, cell coated stents releasing suicide genes, genes inhibiting cell cycle or other critical cellular processes when placed in respiratory tract can prevent the local invasion of the tumor and prevent luminal occlusion and its sequale.

Chemicals and drugs can be added during preparation of the composition. Cells, viruses and labile peptides and growth factors are preferably added to the composition maintained in a liquid state immediately before the composition is applied to a device. Live cells, viruses, peptide or other protein products which can adhere to the composition in the gelled state may also be added to the composition that has been applied to a device The stringency of the cellular attachment to the stent indicates that these devices can be placed in natural passages such as respiratory, gastrointestinal, genitourinary tract using an oscopic approach. With the appropriate cell coated stent any tumor arising from the wall of a luminal organ or adjacent structures can be treated. The coated device would not only treat the primary pathology but would also remove the obstruction to lumen thereby alleviating the symptoms, especially in cholangiocarcinoma and other cancers of the biliary system and luminal organs. Stents or devices of appropriate size and coating can be used to treat gastrointestinal strictures and malignancies. Ureteral and urethral strictures are common following injury due to a ureteric stone, surgery or radiotherapy placement of an epithelized stent can prevent the deleterious effects of the stricture.

The invention also provides a novel method of adhering cells to a medical device. Cells may be added to the composition either before of after the composition is applied to a medical device. In one embodiment, therapeutic cells such as stem cells or genetically engineered cells such as viral-packaging cells or transduced cells that express growth factors, pro-drug processing factors or other therapeutic genes, may be added to the composition prior to application of the composition by mixing the cells with the composition prior to gelling. The resulting composition is applied to the device and the device, after the composition is dried, may be placed in a patient. Preferably, the coated device is dried for 20 minutes at room temperature prior to implantation.

Alternatively, the composition may be applied to the device and the device cultured with the cells and then placed into the patient. Preferably, three layers of the composition are applied to the device as described above prior to culturing the coated device with the cells in an appropriate medium and temperature. Preferably, the coated device is cultured with the cells for 4 hours, moved to a second culture plate with fresh medium and then cultured for 8 to 20 hours, or overnight.

The composition of the invention may also be used as a glue to join tissues, such as adhering skin grafts or gluing fractured bone tissue, or to adhere a membrane or wound closure in place, or as a sealant to stop bleeding or blood flow. For use as glue, a cross-linking agent or polymerising agent is added to the composition prepared as described above prior to gelling. Preferably, the composition is complement-inactivated serum comprising 5% gelatin and 0.01 to 5% formaldehyde, most preferably 0.8% formaldehyde. Glutaraldehyde may also used as the cross-linking or polymerising agent. Glue with a higher hydration rate is obtained by decreasing the serum concentration to about 50% and using 2% formaldehyde. This wetter bioglue is suitable for applications that may require a more flexible, gel-like adhesive. The glue may also be custom designed by using autologus serum. The rigidity and strength of the composition can be adjusted for any particular application by varying the concentration and types of the gelling agent and the cross-linking or polymerising agent. The composition may also be air dried to increase the strength of the resulting glue. As the composition of the invention can polymerise in moist conditions and can be made flexible, the composition provides glue which is flexible in use, in contrast to rigid fibrin glue of the prior art. The composition may be used as a glue and depending in its other uses, in liquid, semi-gelled or gelled state as may be required and as will be appreciated by persons skilled in the art.

By adding a cross-linking or polymerising agent, the composition may be further adapted to provide a solid support such as stents or scaffolding to support tissue or nerve growth or membranes or dressings that may be used to support the growth of skin cells or used as a membrane for tissue grafts or wound closures. A spongy foamed hydrogel that has increased surface area can also be formed by sonicating the composition immediately after addition of the cross-linking or polymerising agent.

To prepare a composition as a solid support, a cross-linking or polymerising agent is added to the composition as described above. Preferably, the cross-linking agent used is an aldehyde cross-linker such as formaldehyde or glutaraldehyde at a concentration of 0.1 to 5%. Most preferably, the composition comprises 2% formaldehyde. The resulting mixture is poured into a shaped cast, for example, a tubular cast that contains a central mandrel, and allowed to polymerise. To form a sheet or a membrane, the mixture is poured out so as to create a thin layer. Any excess cross-linking agent may be removed by washing, preferably 3 times for about 1 hour each, or once for 8 to 20 hours. To prepare a foamed hydrogel, the composition is prepared as described for the forming of the solid support, but the composition is sonicated following the addition of the cross-linking agent. The foamed composition is then cast or moulded into a shape or as membranes. The composition is then cooled on ice to form a sponge like scaffold and may be air, oven or freeze-dried and stored for later use.

The concentration indicated for the cross-linking agent is w/v.

Other features and advantages of the present invention will become apparent from the following examples. It should be understood, however, that the detailed description and the specific examples while indicating preferred embodiments of the invention are given by way of illustration only, since various changes and modifications within the spirit and scope of the invention will become apparent to those skilled in the art from this detailed description.

EXAMPLES

Experiment 1: Coating of Stents to Support Cell Growth or Glue Live Cells

The ability of a stent coated with the composition of the invention to support cell growth was tested using various types of cells. The cell types tested were NIH3T3 mouse fibroblast cells, human umbilical vein endothelial cells (HUV-EC-C), human aortic smooth muscle cells (HA-HSMC) and human mesenchymal stem cells (hMSC) and retroviral packaging cells.

Under sterile conditions a mixture of complement inactivated serum containing 5% gelatin and 250 U/ml heparin was prepared. The gelatin was dissolved by vortexing, followed by heating at 45° C. for 15 minutes.

In one method the composition prepared was coated on to the stent in three layers with drying for 1 hr at 4° C. after the first two coats, and 30 minutes at room temperature after the third coat. The coated stents were then cultured with NIH3T3, HUV-EC-C, HA-HSMC and hMSC cells at a concentration of $10^6$Cells/ml in respective media for 4 hours. The stents were then transferred to a plate with fresh medium and cultured overnight. The cell adherence and growth was visualized under an inverted microscope.

In another method the composition comprising complement inactivated serum and 5% gelatin was prepared by mixing serum and gelatin at 37° C. The composition was maintained at 37° C. until cells (NIH3T3, HUV-EC-C, HA-HSMC and HMSC) were added to the composition. The resulting composition was applied to the stents to form a coat and the coated stent were then cooled and dried at room temperature for 20 min.

Experiment 2: Coated Stents as A Targeted Delivery System for Cells, Genes and Drug Delivery The use of intra-vascular stents in the treatment of arteriosclerosis is frequently complicated by intimal hyperplasia, a pathological process that leads to re-occlusion of the stented blood vessel. Gene therapy is a potential therapeutic approach for the treatment of intimal hyperplasia. However, a major limiting factor of this approach remains in gene delivery to the target site in sufficient concentration. Release of naked DNA from polymer coated controlled release stent resulted in a very low level of transduction and only transient expression of the therapeutic gene. Viral vectors, and particularly retroviral vectors, are very efficient transducing agents. However, we found that the use of retroviral vector alone results in a very low level of transduction, probably due to the very low rate of replication of the smooth muscle cells in the vessels. We have also found that co-culture with viral packaging cells results in a high level of transduction of vascular cells that proliferate at a slow rate. We have utilized this observation to design a new approach for local gene delivery using stents coated with the composition of the invention that supports viral-packaging cells. This approach facilitates local and sustained gene delivery at a very high concentration to the site of interest.

In this experiment, the cells were grown on to the stents as described above except the cells used were retroviral packaging cells (TELCeB6AF or TKMFG46) that had been pretreated with 25 ug/ml mitomycin C for 2 hours. The media used was DMEM containing 10% FCS. Mitomycin C prevents proliferation of packagins cells in vivo. To also induce immunological clearance of these cells in the body, the use of allogenic and xenogenic packaging cells may be used.

The cells were also glued onto balloon-mounted stents by mixing complement-inactivated serum containing 5% gelatin and heparin 150 U/ml with the freshly harvested packaging cells. The resulting composition on gelling was applied to the stents to form a coat. The coated stents were dried for 20 min at room temperature.

The ability to metabolise culture media was used to assess the viability of the cells that were coated on to the stent. The levels of active gene expression and viral vector production was also used as an indicator of cell viability, and determined as follows. Staining for β-gal expression using X-Gal substrate as per the standard protocol (Lau C, Soriano H E, Ledley F D, Finegold M J, Wolfe J H, Birkenmeier E H, Henning S J. Retroviral gene transfer into the intestinal epithelium. Hum Gene Ther 1995; 6:1145-51) was used to assess gene expression in LacZ-expressing packaging cells. The level of transduction of NIH3T3 cells surrounding a cell-coated stent was used to assess the viral vector production. X-Gal staining was used as a measure of transduction in the case of LacZ-expressing vectors and sensitivity to gancyclovir in the case of tk-expressing cells.

The cells grown on coated stents, as well as those glued to the stents instantly, were subjected to shearing stress by forcing PBS through the lumen of the stent. As well, the stent was blown up in vitro using an intraluminal balloon at 10 atm for 5 minutes.

Animal experiments were conducted following the International Guiding Principles For Animal Research. Five Yorkshire pigs weighing 25-30 kg were obtained and were maintained on a normal non-atherogenic diet. Under general anaesthesia coronary angiography was performed followed by balloon angioplasty. Two stents with LacZ-expressing packaging cells attached by growing or gluing were deployed per animal: one in the left anterior descending (LAD) artery and the other in the left circumflex artery (LCX), the site of the prior angioplasty. The animals were maintained on antiplatelet therapy (Ticlopidine 250 mg and aspirin 325 mg) that started 3 days before the procedure and continued through the duration of the experiment until euthanasia. The coronary arteries were harvested at variable time points of 2, 4, 8 and 12 weeks, and fixed in 4% formaldehyde and 0.4% glutaraldehyde for 1 hr, then stained with X-Gal overnight. Eosin counterstaining and histological analysis was done on 10 µm sections of the vessel.

Results

The composition prepared as described gelled on standing. The rate of gelling was directly related to the gelatin concentration and inversely related to temperature. At a gelatin concentration of 5% the mixture gelled in about 30 minutes at room temperature (25° C.). Air-drying enhanced the rate of gelling of the composition. The composition liquefied at 37° C. and above and the rate was inversely related to gelatin concentration and directly related to temperature. The rate of gelling was also affected by the presence of cells since the presence of cells make the composition more viscous, leading to faster gelling rate.

Figure 1:
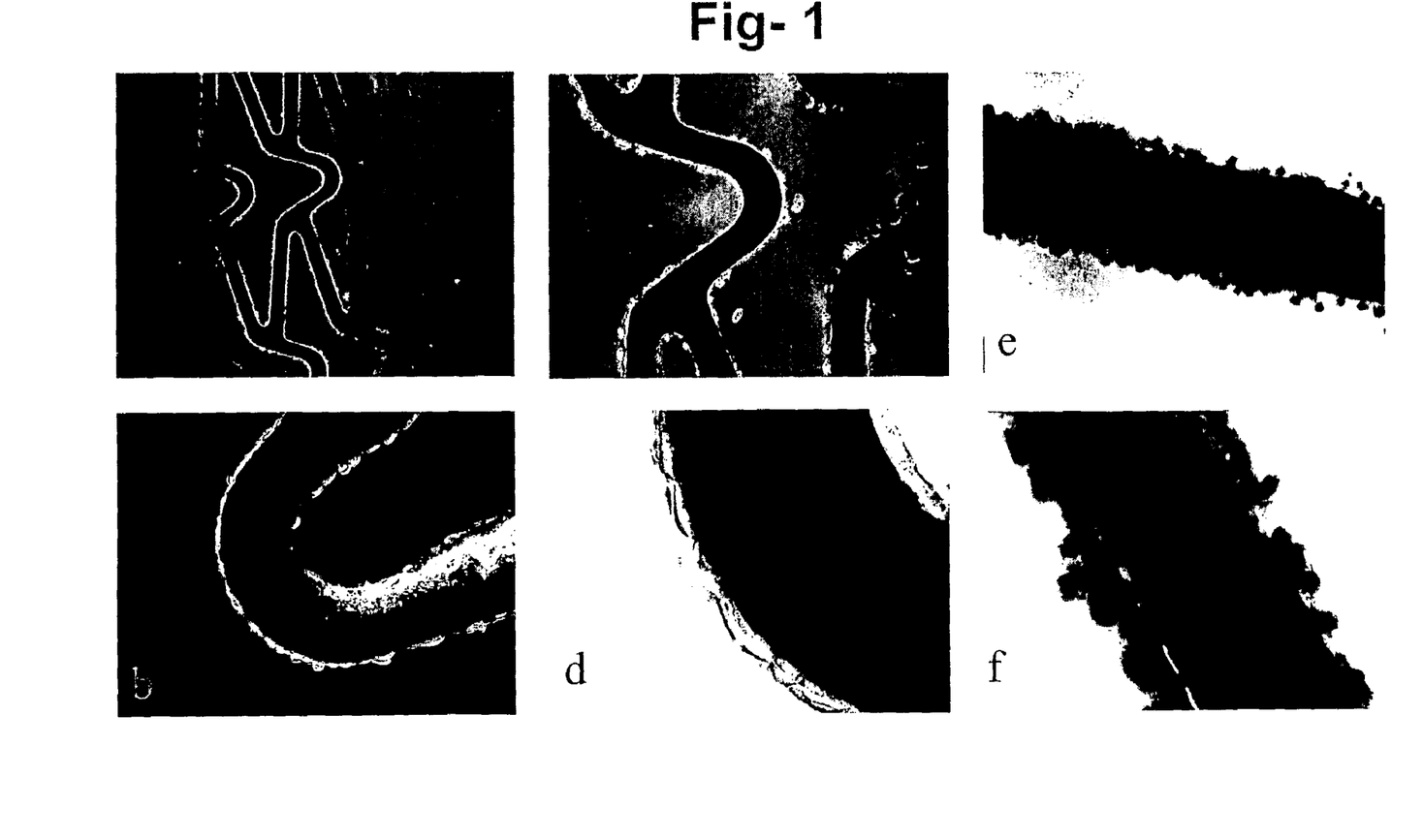
FIG. 1 shows a multi-link stent coated with a composition according to one embodiment of the invention and then cultured with LacZ retroviral packaging cells (TELCeB6AF). These cells produce lacZ retroviral vectors, which carry the lacZ reporter gene. (a) to (d) show unstained cells, (e) and (f) show cells stained for LacZ expression.

The gelled composition supported the growth of cells. FIG. 1(a)-(d) shows a multi-link stent supporting the growth of TELCeB6AF retroviral packaging cells producing MFGnlslacZ retroviral vectors, which carry the lac-Z reporter gene. The cells grew as a monolayer on the stents when seeded at a concentration of $10^6$ cells /ml for 4 hrs with intermittent shaking, followed by transfer to a well with fresh media for 24 hrs. Uncoated stents were unable to support the growth of the cells. The coated stents also supported the growth of mouse fibroblast NIH3T3, human umbilical vein endothelial cells (HUV-EC-C), human smooth muscle cells (HA-HSMC) and TKMFG46 retroviral packaging cells producing the MFGn1s-tk vector, which carries the tk gene.

Figure 2:
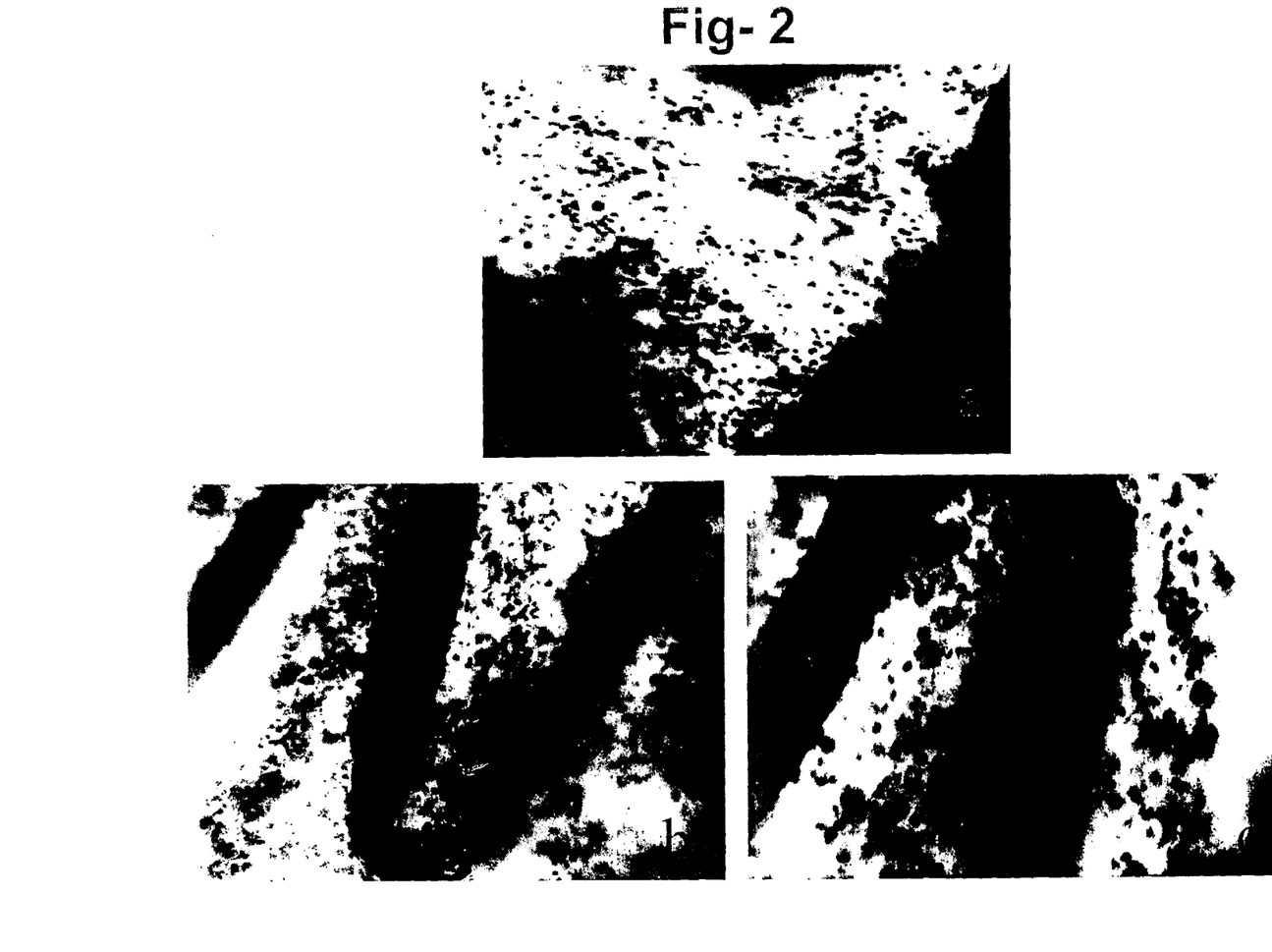
FIG. 2 shows a multi-link stent coated with a composition containing TELCeB6AF in accordance with one embodiment of the invention.

In the second method where the cells were mixed with the composition and then instantly glued onto the balloon-mounted stent, the cells stuck to the stent struts as well as forming a polymeric web between the struts (FIG. 2).

Figure 3:
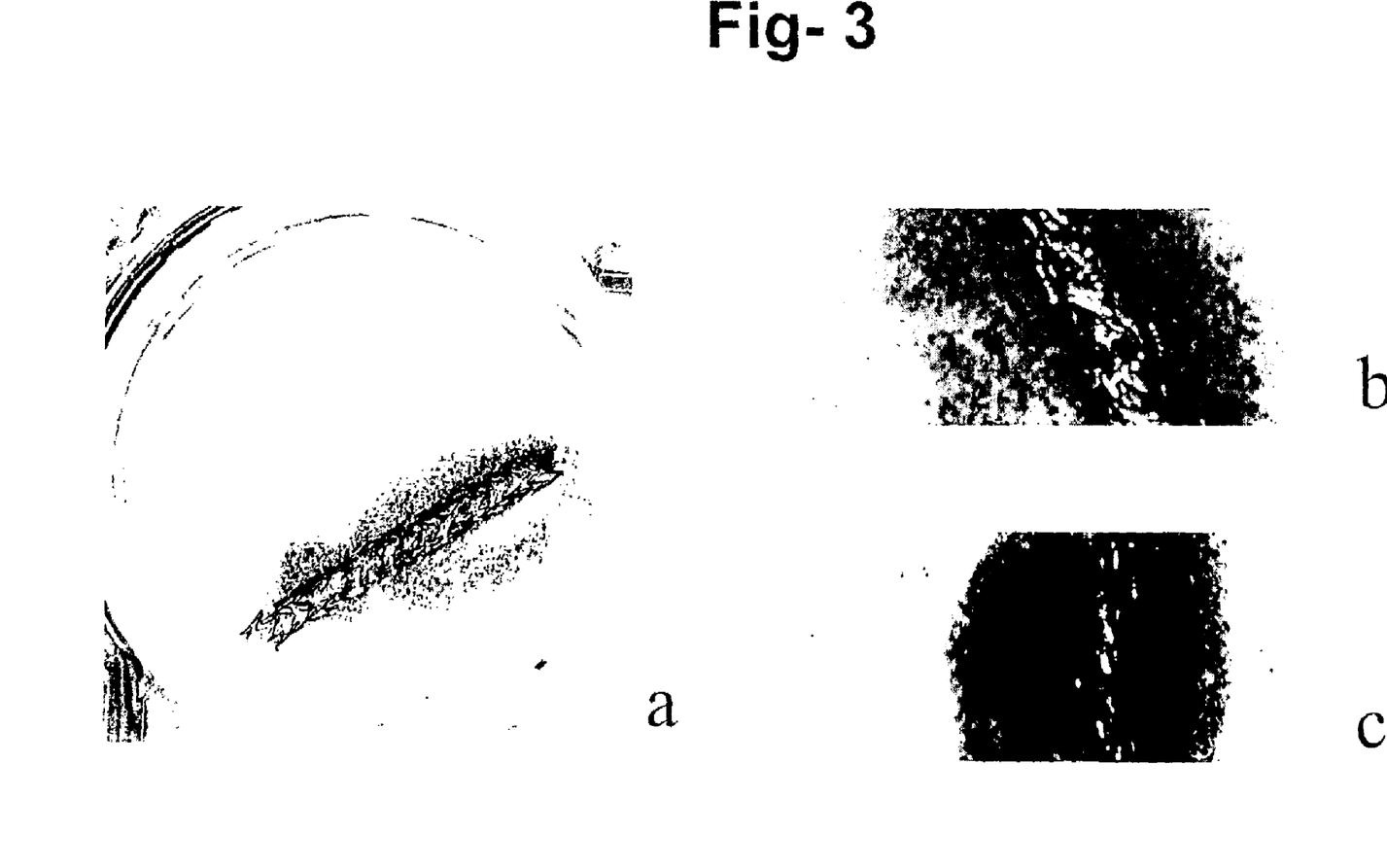
FIG. 3 shows X-Gal staining of NIH3T3 cells that were transduced by placement of a stent coated with TELCeB6AF packaging cells on a bed of NIH3T3 cells.
Figure 4:
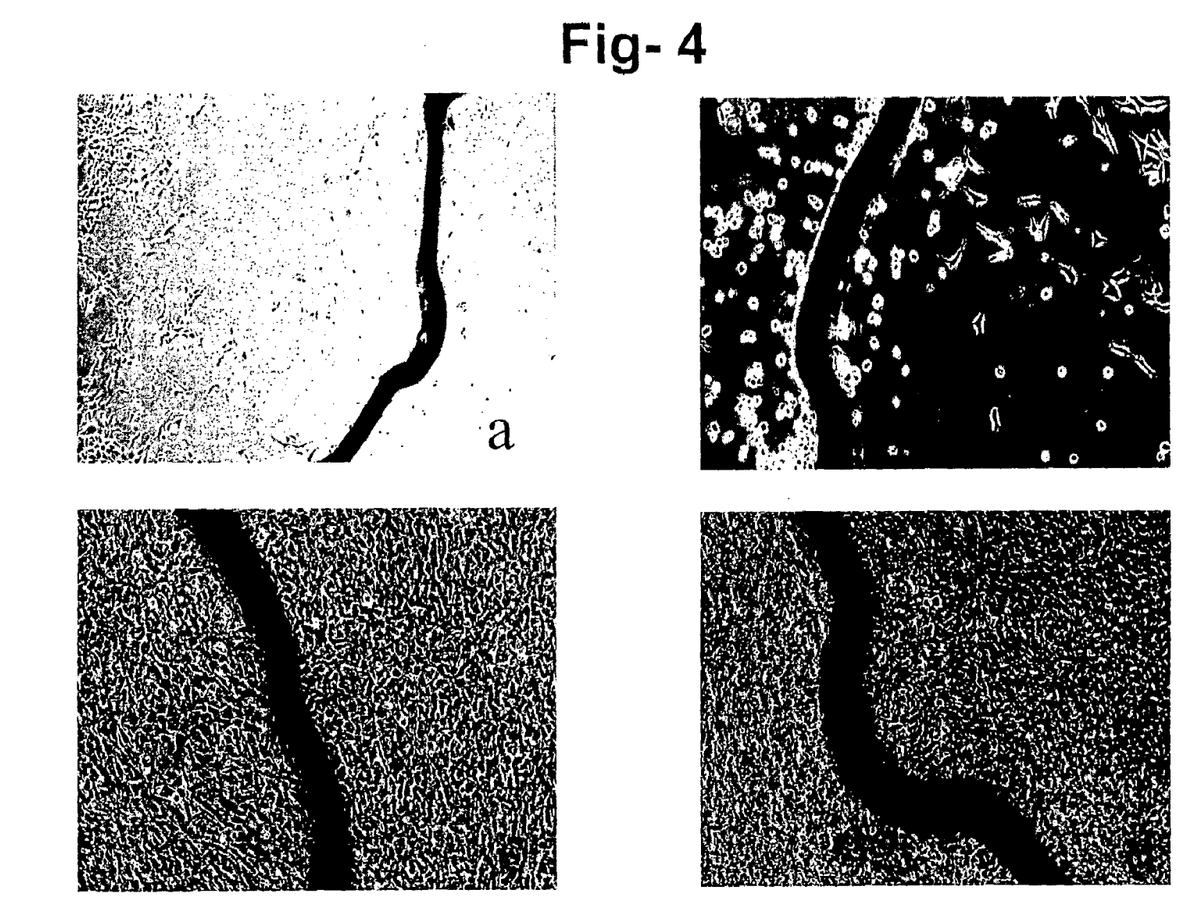
FIG. 4 shows the response of NIH3T3 cells contacted with (a), (b) stents coated with TK retroviral packaging cells (TK- MFG46) expressing the tk gene or (c), (d) uncoated stents, after treatment with gancyclovir.

The cells grown on the stent, as well those glued directly to the stent, were viable and actively metabolised culture media. The cells also expressed their genes in a normal fashion. Retroviral packaging cells encoding the LacZ gene stained positively for β-gal expression on staining with X-Gal solution, thereby indicating normal viability and normal function (FIG. 1(e),(f), FIG. 2). The placement of a stent coated with TELCeB6AF packaging cells on a bed of NIH3T3 fibroblast cells resulted in localised transduction of cells surrounding the stent as indicated by X-Gal staining (FIG. 3), indicating active production of viral vectors that are able to transduce the surrounding fibroblast. Cells further away were not stained indicating the local nature of the spread. The same experiment was repeated with the TKMFG46 retroviral packaging cells expressing the tk gene, followed by gancyclovir treatment, resulting in decreased cell proliferation and cell death in a localised area surrounding the stent (FIG. 4).

In vitro testing of the stringency of binding of the cells to the stent resulted in retention of 50-60% of the cells grown on stents. In the case of cells glued to the stent, 90% survived. The process of balloon expansion of the stent did not cause fragmentation of the polymeric biomaterial web, thereby indicating the flexibility of the biomaterial.

Figure 5:
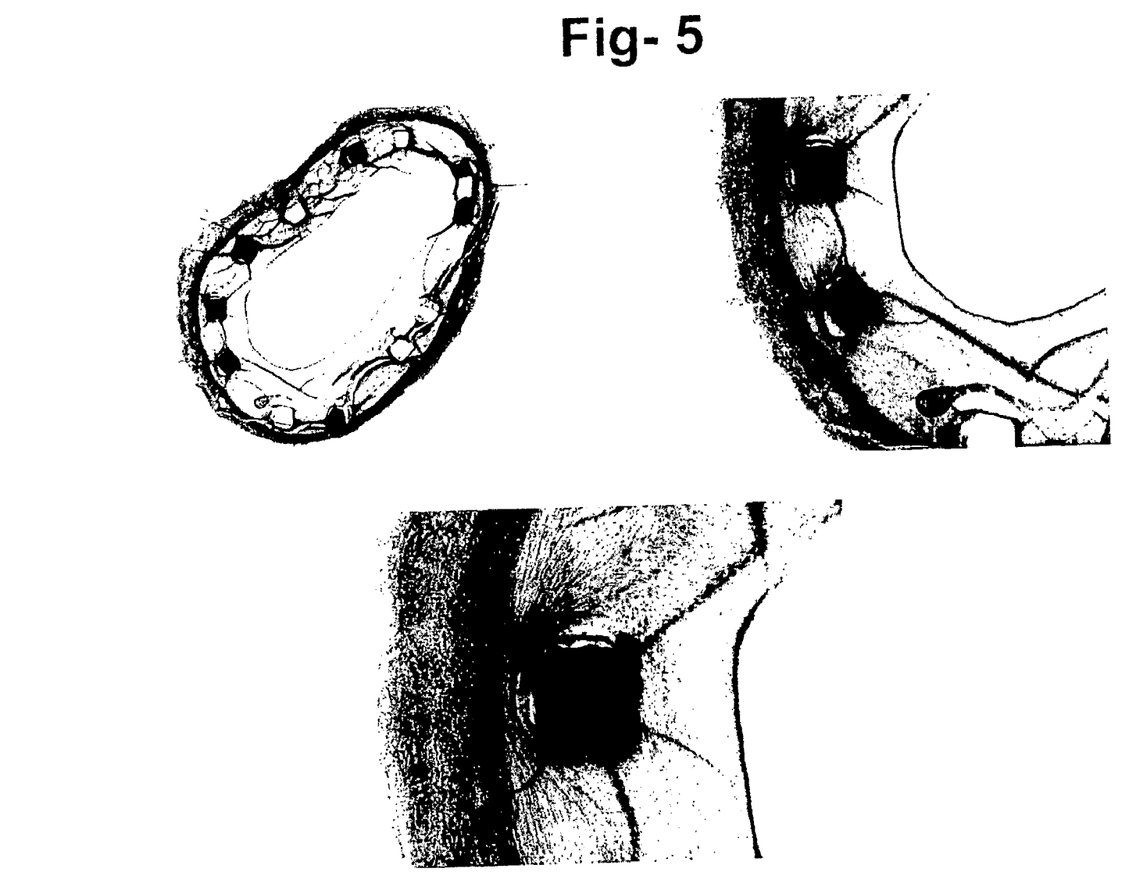
FIG. 5 shows histological sections of X-Gal stained pig coronary arteries that received TELCeB6AF packaging cells grown on stent (as described in Experiment 1).
Figure 6:
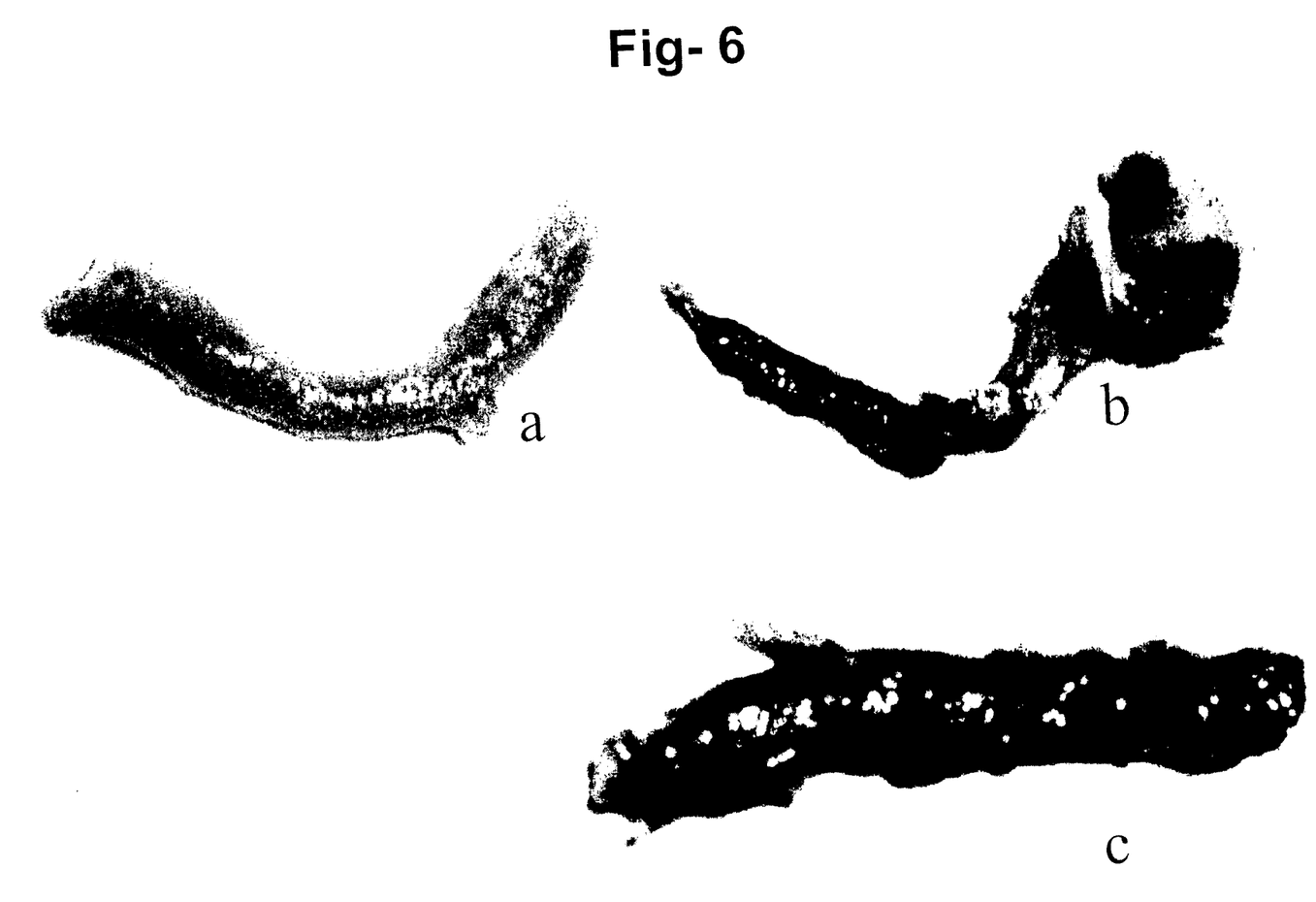
FIG. 6 shows the X-Gal stained coronary arteries that received TELCeB6AF packaging cells glued to stent (as described in Experiment 1).
Figure 7:
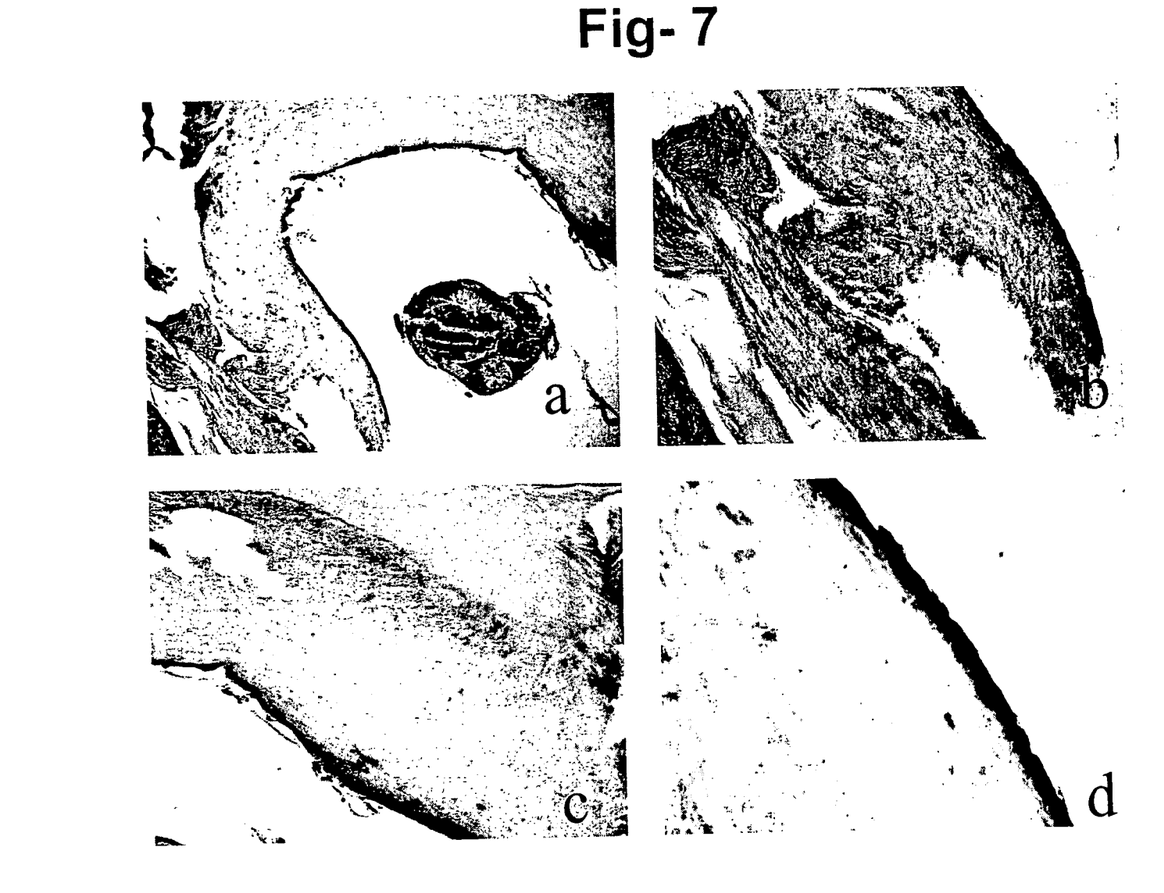
FIGS. 7 and 8 show histological sections of X-Gal stained pig coronary arteries four weeks (FIG. 7) and 12 weeks (FIG. 8) after implantation of stent coated with TELCeB6AF packaging cells.
Figure 8:
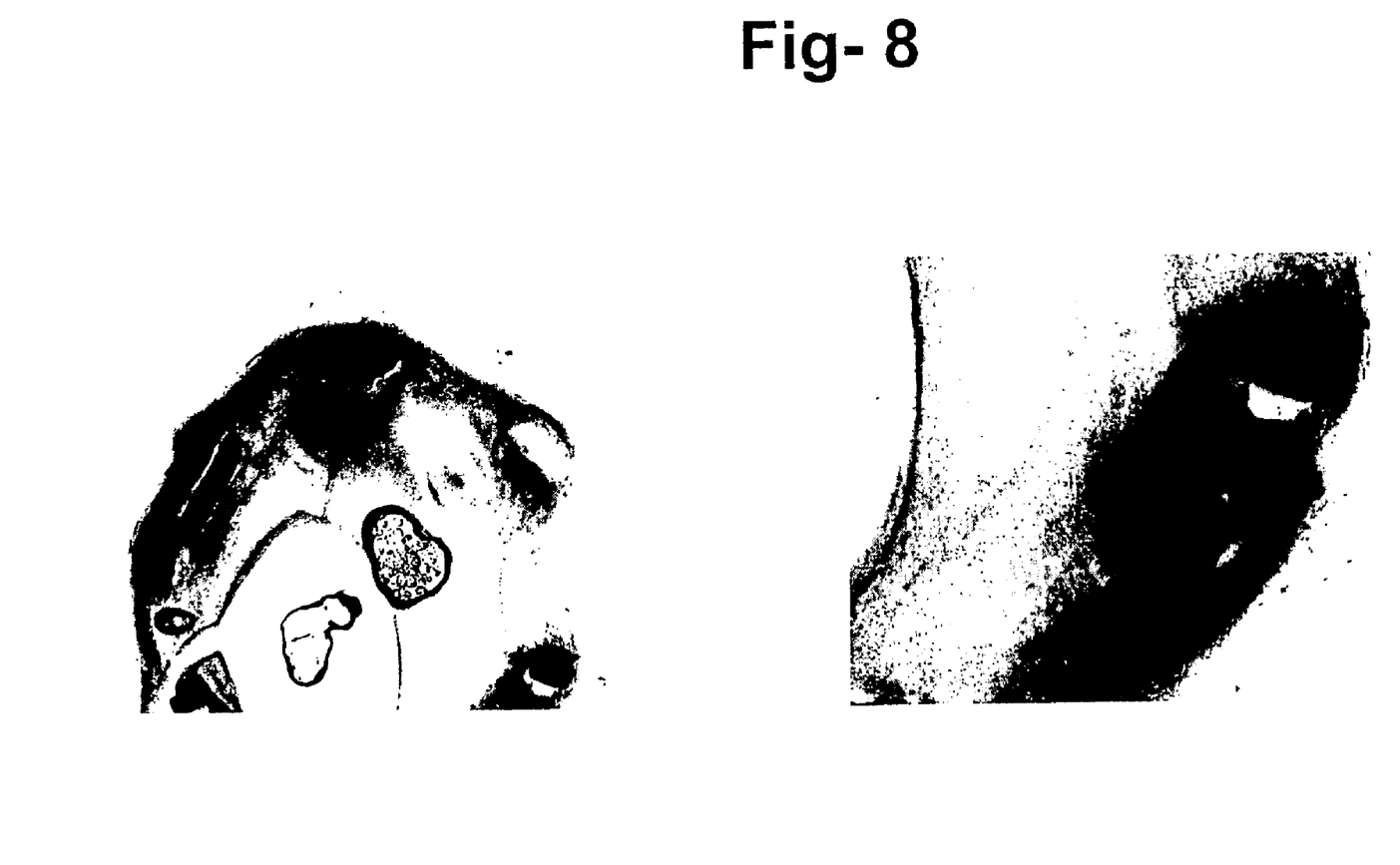

All the coronary vessels that were stented with LacZ-expressing packaging cells stained positive upon staining with X-Gal. The coronary arteries that served as control did not show any staining. The vessels of the 2 pigs with cells grown on the stent were harvested at 8 and 12 weeks and showed positive staining that was mostly limited to the stented areas with a minimal extension to the adjacent area of the vessel (FIG. 5). The vessels of the 4 pigs (latest data) with cells glued to the stent were harvested at 4, 6, 8 and 12 weeks respectively. The vessels showed intense blue staining with X-Gal at the stented area that extended for a few millimetres into the adjacent areas of the vessels. The vessels further down and up were not stained (FIG. 6). Histological examination of the vessels showed staining in all layers of the vessel but predominantly in the media and the endothelium (FIG. 7).

As the results demonstrate, the invention successfully transfers genes to the targeted vascular site in high concentration. The success of local gene delivery system generally depends on the type of transducing agent being used, ability of the agent to stay on the devise for an extended period of time in a high pressure and flow environment and finally on the ability to induce a sustained gene expression. Additionally the devise and the coating material should not aggravate the intimal proliferation.

Remodelling and restenosis is a long-term process, which continues up to 3 years (Teirstein PS et.al. 2000). Therefore long term expression of the therapeutic agent would be required to address this problem. Retroviral vectors are ideal for long-term expression and due to their ability to selectively transduce only the dividing cells, would target only the cells of interest.

The present invention allowed sustained and high concentration release of the vector of interest at the local site, compared to devices coated only with vector alone. Another important advantage of this system is that the composition when coated onto the device can also act as a barrier protecting the underlying denuded surface in cases of angioplasty induced injury and decrease incidence of acute thrombosis. The rate of vector release from the cells transferred to the implant site can also be controlled after stent implantation by using a suitable promoter or cellular marker gene. In the porcine intra-coronary stent model, acute thrombosis did not occur and angiographic data also did not show any significant narrowing of the lumen of the stented vessel. The composition of the invention is unique in that the primary component, serum, can be autologous thereby minimizing any incompatibility. Moreover, use of complement free serum and the presence of heparin reduce the risk of inflammation and thrombosis.

The vector gene was expressed in all the layers of the vessel of the local site with the predominant expression, in the medial layer, due to maximum cell proliferation in this layer during neointima formation and the ability of the retroviral vectors to selectively transduce only dividing cells. The transgene expression was observed for at least 12 weeks and the invention therefore also provides sustained local expression of therapeutic gene for a long time. The lack of any adverse effect on the patency of the vessel as well as the myocardium also indicates the composition of the invention is safe and biocompatible.

These cell-coated stents can also function as a vehicle for cell transplantation, for the initiation of processes like endothelization and epithelization. The composition of the invention not only support growth of cell but their survival when glued to a device in the absence of culture media and as such may be particularly useful in stem cell plantation.

Experiment 3—Composition as a Skin Dressing and Scaffold to Grow Skin.

Gelatin at a concentration ranging from 1 to 40% preferably 5% to 10% is dissolved in autologus or hetrologus serum (50 to 100% concentration) by vortexing followed by heating at 45° C. for 15 min there after cooling to 37° C. Keeping the mixture in liquid state additives such as heparin, drugs or factors can be added. The mixture is then polymerised using a cross-linking agent. The concentration of cross-linking agent used is low and is generally not toxic to cells when it is added to cells maintained in a culture media. Following the addition of cross-linking agent the mixture is vortexed rapidly and poured into a petridish and spread evenly. The material polymerised in a few seconds to minutes depending on the concentration. Excess cross-linking agent can be removed by washing with PBS 3×1 hr each. In conditions involving use of high concentration of polymerising agent overnight washing can be done. The material formed is stable and does not dissociate rapidly when maintained in culture media. The membranous material is flexible, elastic and can be used as a biological dressing or used to grow cells such as fibroblasts for use as skin scaffold.

Experiment 4—Composition as a Bioglue

Various different combinations, each with different polymerisation capacity, hydration and strength were prepared as biological glue.

Under sterile conditions a mixture of complement inactivated serum containing 2-20% gelatin and was prepared. The gelatin was dissolved by vortexing followed by heating at 45° C. for 15 min there after it was allowed to cool and maintained at 37° C. To the material a polymerising agent was added and vortexed instantly followed by application to the tissue to be glued.

A mixture combining serum, 5% gelatin and formaldehyde (0.01-5%) resulted in polymerisation of the material into a sticky semisolid to solid material. The rate of polymerisation depended on the concentration of the formaldehyde. At a concentration of 0.8% formaldehyde (or 0.2% glutaraldehyde), the mixture started to polymerise instantly in 5-10sec and formed a sticky semi solid material in under a minute. The material was able to glue plastic, glass, wood and bone. Air-drying of the material further strengthened the material.

A mixture combining serum, 10% gelatin and formaldehyde 0.4% resulted in faster polymerisation of the material into a sticky semisolid to solid material. Indicating the dependence of the polymerisation rate on gelatin concentration. The material formed was also stronger.

A mixture of combination 50% diluted serum, 5% gelatin and formaldehyde 2% also resulted in a very faster polymerisation of the material into a sticky semisolid to solid material. The material was more hydrated and could be applied in situation requiring higher hydration state.

Experiment 5—Composition as a Solid Scaffold

Under sterile conditions a mixture of complement inactivated serum containing 2-20% gelatin preferably 5%-10% was prepared. The gelatin was dissolved by vortexing followed by heating at 45° C. for 15 min there after it was allowed to cool and maintained at 37° C. To the material a polymerising agent such as formaldehyde at concentration between 0.1 to 5% was added and vortexed instantly followed by transfer to a tubular cast containing a central mandrel and cooling at room temperature. The tubular scaffold can be used to bridge sectioned nerves. It can also be used in other settings requiring a tubular scaffold.

Experiment 6—Composition as a Foamed Hydrogel-like Scaffold

Under sterile conditions a mixture of complement inactivated serum containing 2-20% gelatin preferably 5%-10% was prepared. The gelatin was dissolved by vortexing followed by heating at 45° C. for 15 min there after it was allowed to cool and maintained at 37° C. To the material a polymerising agent such as formaldehyde at concentration between 0.1 to 5% was added and vortexed instantly followed by sonication for 10-15 sec to form foam like material, which was poured onto a tubular cast containing a central mandrel. The mixture was instantly cooled on ice to form a sponge like scaffold with a large surface area. Similar results were obtained with other cross-linking agents such as glutaraldehyde. The material can be air, oven or freeze dried and stored for later use. The material can also be cast as membranes that would have a large surface area of the foamy composition.

All documents referred to herein are fully incorporated by reference.

What is claimed is:

1. A composition comprising about 25 to 150% (v/v) complement-inactivated serum, a cross-linking agent and a gelling agent in an amount sufficient to allow the composition to gel, wherein the gelling agent is different from the cross-linking agent and is in a liquid form prior to gelling of the composition, the composition being a glue, dressing, membrane, scaffold or hydrogel.

2. The composition according to claim 1 wherein the serum is complement-inactivated human blood serum.

3. The composition according to claim 2 wherein the gelling agent is gelatin.

4. The composition according to claim 3 comprising about 25 to 150% (v/v) serum and about 0.1 to 40% (w/v) gelatin.

5. The composition according to claim 4 comprising about 2 to 10% (w/v) gelatin.

6. The composition according to claim 5 wherein the serum is autologous.

7. The composition according to claim 6 further comprising an anticoagulant.

8. The composition according to claim 7 wherein the anticoagulant is heparin.

9. The composition according to claim 8 comprising 250 U heparin/ml of the composition prior to gelling.

10. The composition according to claim 9 which is a vehicle for delivery of a therapeutic product.

11. The composition according to claim 10 wherein the therapeutic product is a retroviral packaging cell transfected with a retroviral vector.

12. The composition according to claim 3 comprising about 50 to 100% (v/v) serum and about 1 to 40% (w/v) gelatin.

13. The composition according to claim 1 wherein the cross-linking agent is formaldehyde or glutaraldehyde.

14. The composition according to claim 13 comprising about 0.01 to 5% (w/v) formaldehyde.

15. The composition according to claim 14 wherein the glue comprises 50% (v/v) serum, 5% (w/v) gelatin and 2% (w/v) formaldehyde.

16. The composition according to claim 14 wherein the glue is complement-inactivated serum comprising 5% (w/v) gelatin and 0.8% (w/v) formaldehyde.

17. The composition according to claim 14 wherein the scaffold or hydrogel is complement-inactivated serum comprising 5 to 10% (w/v) gelatin and 0.1 to 5% (w/v) formaldehyde.

18. The composition according to claim 1, wherein the composition is a glue.

19. The composition according to claim 18 wherein the serum is complement-inactivated human blood serum.

20. The composition according to claim 18 wherein the gelling agent is gelatin.

21. The composition according to claim 18 wherein the cross-linking agent is formaldehyde or glutaraldehyde.

22. The composition according to claim 18 comprising about 0.01 to 5% (w/v) formaldehyde.

23. The composition according to claim 18 wherein the glue comprises 50% (v/v) serum, 5% (w/v) gelatin and 2% (w/v) formaldehyde.

24. The composition according to claim 18 wherein the glue is complement-inactivated serum comprising 5% (w/v) gelatin and 0.8% (w/v) formaldehyde.

25. The composition according to claim 1, wherein the composition is a dressing.

26. The composition according to claim 25 wherein the serum is complement-inactivated human blood serum.

27. The composition according to claim 25 wherein the gelling agent is gelatin.

28. The composition according to claim 25 wherein the cross-linking agent is formaldehyde or glutaraldehyde.

29. The composition according to claim 25 comprising about 0.01 to 5% (w/v) formaldehyde.

30. The composition according to claim 1, wherein the composition is a membrane.

31. The composition according to claim 30 wherein the serum is complement-inactivated human blood serum.

32. The composition according to claim 30 wherein the gelling agent is gelatin.

33. The composition according to claim 30 wherein the cross-linking agent is formaldehyde or glutaraldehyde.

34. The composition according to claim 30 comprising about 0.01 to 5% (w/v) formaldehyde.

35. The composition according to claim 1, wherein the composition is a scaffold.

36. The composition according to claim 35 wherein the serum is complement-inactivated human blood serum.

37. The composition according to claim 35 wherein the gelling agent is gelatin.

38. The composition according to claim 35 wherein the cross-linking agent is formaldehyde or glutaraldehyde.

39. The composition according to claim 35 comprising about 0.01 to 5% (w/v) formaldehyde.

40. The composition according to claim 35 wherein the scaffold is complement-inactivated serum comprising 5 to 10% (w/v) gelatin and 0.1 to 5% (w/v) formaldehyde.

41. The composition according to claim 1, wherein the composition is a hydrogel.

42. The composition according to claim 41 wherein the serum is complement-inactivated human blood serum.

43. The composition according to claim 41 wherein the gelling agent is gelatin.

44. The composition according to claim 41 wherein the cross-linking agent is formaldehyde or glutaraldehyde.

45. The composition according to claim 41 comprising about 0.01 to 5% (w/v) formaldehyde.

46. The composition according to claim 41 wherein the hydrogel is complement-inactivated serum comprising 5 to 10% (w/v) gelatin and 0.1 to 5% (w/v) formaldehyde.

* * * * *